(12) United States Patent
Taylor et al.

(10) Patent No.: US 10,039,530 B2
(45) Date of Patent: Aug. 7, 2018

(54) INTERFEROMETRIC FORCE SENSOR FOR SURGICAL INSTRUMENTS

(71) Applicant: The Johns Hopkins University, Baltimore, MD (US)

(72) Inventors: Russell H. Taylor, Severna Park, MD (US); Iulian Iordachita, Lutherville-Timonium, MD (US); Jin U. Kang, Ellicott City, MD (US); Xuan Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 190 days.

(21) Appl. No.: 14/973,823

(22) Filed: Dec. 18, 2015

(65) Prior Publication Data

US 2016/0100906 A1    Apr. 14, 2016

Related U.S. Application Data

(63) Continuation of application No. 13/810,183, filed as application No. PCT/US2011/044724 on Jul. 20, 2011, now Pat. No. 9,241,693.

(Continued)

(51) Int. Cl.
*A61B 17/00* (2006.01)
*A61F 9/007* (2006.01)
(Continued)

(52) U.S. Cl.
CPC .............. *A61B 17/00* (2013.01); *A61B 19/46* (2013.01); *A61B 19/5244* (2013.01);
(Continued)

(58) Field of Classification Search
CPC ... A61B 17/00; A61B 19/46; A61B 2019/466; A61B 2019/5261; A61B 2016/464; G01K 3/26
See application file for complete search history.

(56) References Cited

U.S. PATENT DOCUMENTS 5,951,881 A    9/1999    Rogers et al.
6,014,215 A    1/2000    Kempen et al.
(Continued)

FOREIGN PATENT DOCUMENTS

CN    1045028 A       9/1990
WO    WO-90/09141 A2  8/1990
WO    WO-98/38907 A1  9/1998

OTHER PUBLICATIONS

Akinbiyi et al., "Dynamic Augmented Reality for Sensory Substitution in Robot-Assisted Surgical Systems", in *28th Annual International Conference of the IEEE Engineering in Medicine and Biology Society,*, 2006, pp. 567-570.

Akinbiyi, *Intelligent instruments and visual force feedback in laparoscopic minimally invasive surger*, thesis in Mechanical Engineering, The Johns Hopkins University, Baltimore, MD, 2005.

(Continued)

*Primary Examiner* — Bradley J Osinski
(74) *Attorney, Agent, or Firm* — Venable, LLP; Henry J. Daley; Xin Gao

(57) ABSTRACT

A surgical tool system according to an embodiment of the current invention includes a surgical tool, and an interferometry system optically coupled to the surgical tool. The surgical tool includes a body section, a sensor section at least one of attached to or integral with the body section, and a surgical section at least one of attached to or integral with the sensor section at an opposing end of the sensor section from the body section. The sensor section comprises an interferometric optical sensor defining a reference distance that changes in response to at least one of a force or a torque when applied to the surgical section of the surgical tool.

27 Claims, 11 Drawing Sheets

Related U.S. Application Data

(60) Provisional application No. 61/365,995, filed on Jul. 20, 2010.

(51) Int. Cl.

| | | |
|---|---|---|
| *A61B 19/00* | (2006.01) | |
| *A61B 17/34* | (2006.01) | |
| *A61B 17/30* | (2006.01) | |
| *G01J 3/26* | (2006.01) | |
| *A61B 90/00* | (2016.01) | |
| *A61B 34/20* | (2016.01) | |

(52) U.S. Cl.
CPC .............. *A61B 90/06* (2016.02); *A61F 9/007* (2013.01); *A61B 17/3478* (2013.01); *A61B 2017/00084* (2013.01); *A61B 2017/00986* (2013.01); *A61B 2017/305* (2013.01); *A61B 2019/465* (2013.01); *A61B 2019/466* (2013.01); *A61B 2019/5261* (2013.01); *A61B 2034/2061* (2016.02); *A61B 2090/064* (2016.02); *A61B 2090/066* (2016.02); *G01J 3/26* (2013.01)

(56) References Cited

U.S. PATENT DOCUMENTS

| | | | |
|---|---|---|---|
| 7,204,844 | B2 | 4/2007 | Jensen et al. |
| 2003/0069522 | A1 | 4/2003 | Jacobsen et al. |
| 2006/0146336 | A1 | 7/2006 | Hauger |
| 2006/0200049 | A1* | 9/2006 | Leo .................... A61B 90/06 600/587 |
| 2007/0156019 | A1 | 7/2007 | Larkin et al. |
| 2008/0294144 | A1 | 11/2008 | Leo et al. |
| 2009/0157092 | A1 | 6/2009 | Blumenkranz et al. |

OTHER PUBLICATIONS

Balicki et al., "Micro-force Sensing in Robot Assisted Membrane Peeling for Vitreoretinal Surgery", in Medical Image Computing and Computer-Assisted Intervention (MICCAI),Beijing,Sep. 2010, p. to appear.
Balicki et al., "Single Fiber Optical Coherence Tomography Microsurgical Instruments for Computer and Robot-Assisted Retinal Surgery", in *Medical Image Computing and Computer Assisted Surgery* (*MICCAI 2009*), London 2009, pp. 108-115. PMID: Pending.
Berkelman et al., "A miniature microsurgical instrument tip force sensor for enhanced force feedback during robot-assisted manipulation", *IEEE T. Robotics and Automation*, vol. 19- 5, pp. 917-922, Oct. 2003.
Berkelman et al., "Performance Evaluation of a Cooperative Manipulation Microsurgical Assistant Robot Applied to Stapedotomy", in *Medical Image Computing and Computer-Assisted Interventions* (*MICCAI 2001*), Utrecht, 2001, pp. 1426-1429.
Bethea et al., "Application of Haptic Feedback to Robotic Surgery",Journal of Laparoendoscopic and Advanced Surgical Techniques, vol. 14-3, pp. 191-195, 2004.
Desai, "Design and Development of a 3-Axis MRI-compatible Force Sensor", in *ICRA 2010 Workshop on Medical Cyber-Physical Systems* Anchorage, May 7. 2010, p. (Abstract in Electronic Proceedings).
Fischer et al., "Ischemia and Force Sensing Surgical Instruments for Augmenting Available Surgeon Information", in *IEEE International Conference on Biomedical Robotics and Biomechatronics—BioRob 2006*, Pisa, Italy, 2006.
Geib, *Multiplexing of Extrinsic Fabry-Perot Optical Fiber Sensors for Strain Measurements*, thesis in Electrical Engineering, Virginia Polytechnic Institute and State University, 2003.
Gupta et al., "Surgical Forces and Tactile Perception During Retinal Microsurgery", in Proceedings of the Second International Conference on Medical Image Computing and Computer-Assisted Intervention (MICCAI 99), Cambridge, England, 1999, pp. 1218-1225.
Gupta, A Method to Enhance Microsurgical Tactile Perception and Performance Through the Use of Auditory Sensory Perception, thesis in M.S. in Engineering, The Johns Hopkins University, Baltimore, 2001.
He, Force Sensing Tool for Retinal Surgery, MS thesis in Mechanical Engineering (MiMed), T. U. Munich, Munich, 2009.
Heijmans et al., "Optical fiber sensors for medical applications—Practical engineering considerations", in 4th European Conference of the International Federation for Medical and Biological Engineering ECIFMBE, Antwerp, Belgium,Nov. 23-27, 2008.
International Search Report and Written Opinion of PCT/US2011/044724.
Iordachita et al., "A sub-millimetric, 0.25 mN resolution fully integrated fiber-optic force-sensing tool for retinal microsurgery", Intl Computer Assisted Radiology and Surgery, vol. 4-4, pp. 383-390, 2009 PMID: 20033585.
Jagtap et al., "Applied Force during Vitreoretinal Microsurgery with Handheld Instruments", in Proc. 26th IEEE Engineering in Medicine and Biology Conference (EMBS), San Francisco, 2004, pp. 2771-2773.
Jan Peirsa et al., "A micro optical force sensor for force feedback during minimally invasive robotic surgery", Sensors and Actuators A: Physical, vol. 115-2-3, pp. 447-455, Sep. 21, 2004.
Jensen et al., "Quantification of microsurgical tactile perception", in The First Joint Meeting of BMES and EMBS, Atlanta, 1999.
Kang et al., "Fourier Domain common-path fiber OCT with tunable reference: analysis and optimization", OSA Technical Digest, CLEO, p. jtuA55, 2007.
Kitagawa et al., "Effect of Sensory Substitution on Suture Manipulation Forces for Surgical Teleoperation," in Medicine Meets Virtual Reality 12, 2004, pp. 157-163.
Kumar et al., "Preliminary Experiments in Cooperative Human/Robot Force Control for Robot Assisted Microsurgical Manipulation", in IEEE Conference on Robotics and Automation, San Francisco, 2000, pp. 610-617.
Liu et al., "Progress toward inexpensive endoscopic high-resolution common-path OCT", in SPIE Conf on Optical Fibers and Sensors for Medical Diagnostics and Treatment Applications X, 2010.
Mueller et al., "Realization of a fiber-optic force-torque sensor with six degrees of freedom", in Proc. SPIE—Optomechatronic Technologies, San Diego, CA,Nov. 17, 2008, pp. 72660S-1 to 72660S-8. http://dx.doi.org/10.1117/12.807141.
Prasad et al., "A Modular 2-DOF Force-Sensing Instrument for Laparoscopic Surgery", in *Proceedings of the Sixth International Conference on Medical Image Computing and Computer Assisted Intervention—MICCAI 2003*, Montreal, 2003, pp. 279-286.
Puangmali et al., "Optical fiber sensor for soft tissue investigation during minimally invasive surgery", in *IEEE Conference on Robotics and Automation* (*ICRA*), Pasadena, CA,May 19-23, 2008, pp. 2934-2939.
Rothbaum et al., "Robot-assisted stapedotomy: micropick fenestration of the stapes footplate", *Otolaryngology—Head and Neck Surgery*, vol. 127-5, pp. 417-426, Nov. 2002.
Rothbaum et al., "Task Performance in stapedotomy: Comparison between surgeons of different experience levels", Otolaryngology—Head and Neck Surgery, vol. 128- 1, pp. 71-77, Jan. 2003.
Sun et al., "Development and Preliminary Data of Novel Integrated Optical Micro-Force Sensing Tools for Retinal Microsurgery", in *IEEE International Conference on Robotics and Automation—ICRA 2009*, Kobe, Japan, 2009, pp. 1897-1902.
Tada et al., "An MR-Compatible Optical Force Sensor for Human Function Modeling", in *Medical Image Computing and Computer-Assisted Intervention—MICCAI 2004*, St. Malo, France,Sep. 2004, pp. 129-136.

* cited by examiner

INTERFEROMETRIC FORCE SENSOR FOR SURGICAL INSTRUMENTS

CROSS-REFERENCE OF RELATED APPLICATION

This application is a Continuation of U.S. patent application Ser. No. 13/810,183 now issued as U.S. Pat. No. 9,241,693, filed Jan. 14, 2013, the entire contents of which are hereby incorporated by reference. U.S. patent application Ser. No. 13/810,183 is a national stage application under 35 U.S.C. § 371 of PCT/US2011/044724, filed Jul. 20, 2011, the entire contents of which are incorporated herein by reference. This application claims priority to U.S. Provisional Application No. 61/365,995 filed Jul. 20, 2010, the entire contents of which are hereby incorporated by reference.

This invention was made with government support under 1R01 EB 007969-01 awarded by the Department of Health and Human Services, the National Institutes of Health. The government has certain rights in the invention.

BACKGROUND

1. Field of Invention

The field of the currently claimed embodiments of this invention relates to surgical instruments and systems that incorporate the surgical instruments, and more particularly to systems and surgical instruments that have integrated force sensors.

2. Discussion of Related Art

In current practice, retinal surgery is performed under an operating microscope with free-hand instrumentation. Human limitations include an inability to clearly view surgical targets, physiological hand tremor, and lack of tactile feedback in tool-to-tissue interactions. In addition, tool limitations, such as lack of proximity sensing or smart functions, are important factors that contribute to surgical risk and reduce the likelihood of achieving surgical goals. Current instruments do not provide physiological or even basic interpretive information, e.g. the force exerted by the instrument on the retinal tissues. Surgical outcomes (both success and failure) are limited, in part, by technical hurdles that cannot be overcome by conventional instrumentation.

The tool-to-tissue interaction forces commonly encountered in retinal microsurgery are generally far below human perceptual limits [1-4]. If too much force is exerted on the retina, then it may be damaged. Typically, surgeons rely entirely on visual appreciation of tissue deformation to estimate how close tool-to-tissue forces are approaching to unacceptable limits. However, this skill is not easily learned and making such estimates is difficult even for an extremely skilled surgeon. Similar challenges may be found in other microsurgical disciplines, including non-retinal ophthalmic surgery, neurosurgery, otologic surgery [6-9], micro-vascular surgery, etc. Even in surgical situations where the actual tool-to-tissue forces may be larger than encountered in microsurgery, such as endoscopic surgery, the tool-to-tissue forces may be difficult to measure or for the surgeon to appreciate directly, due to friction, mechanical constraints, manipulation limitations, etc. These considerations have led a number of researchers to consider methods for incorporating force sensors into surgical instruments. This force information may be used in various ways to assist the surgeon, including use in "sensory substitution" (e.g., [1, 3, 10-12]), in various forms of haptic feedback (e.g., [10, 15]), or otherwise incorporated into control of robotic devices (e.g., [10, 16]).

For example, in retinal surgery (FIG. 1) the surgical tool is inserted through the sclera into the eye to perform the manipulations of delicate tissue during the retinal surgery. To measure the forces exerted between the tissue and the tool tip is very challenging. The force sensing instrument should be capable of measuring the tissue-to-tool force in three dimensions with sub-millinewton resolution. The sensor should be placed possibly close to the tool tip inside of the eye to avoid disturbance of sclera-to-tool forces. Thus the sensor must possess the essential small size so that it can be integrated into the instrument with sub-millimeter diameter. Further requirements include biocompatibility, sterilizability and immunity to electrical noise.

One method for measuring tool-tissue forces is incorporation of a (typically, multiple degree-of-freedom) force sensor into the handle of a surgical tool. This method has been applied for microsurgical force sensing experiments (e.g., [4, 9]). However, in cases such as retinal surgery, where tool-to-sclera interaction forces can be as large as or larger than tool-to-tissue interaction forces, this approach has serious drawbacks. Consequently, there has been interest in developing microsurgical force sensors placed on the distal portion of the surgical tool, below the insertion through the sclera [13, 14]. Although some similar approaches (e.g., [17-19]) have been undertaken for laparoscopic tools, where tool-to-trocar forces can similarly mask tool-to-tissue forces, the challenge for micro-retinal surgery, where the tool shaft diameters can be 0.5-0.7 mm or even smaller, is especially severe. Some early work at Johns Hopkins [1] used a strain gauge mounted on a tool shaft to measure 1 degree-of-freedom (DOF) forces deflecting the tool in "open" experiments on dissected pig retinas, but this tool was not practical for insertion through the sclera. Further approaches include incorporation of electrical sensors (such as strain gauges) into tiny microsurgical instruments.

There have been several optical fiber force sensors proposed for surgical applications (e.g., [13, 14, 20-23]), as well as several other optical approaches (e.g., [24, 25]) for surgical force sensing. These sensors use a variety of physical principles, including modifications in reflected or transmitted light intensity, changes in polarization, fiber-Bragg grating (FBG) sensing, etc. FBG sensors are constructed by producing a modulation of the index of refraction (i.e., a "grating") along the length of an optical fiber [20]. Stretching the fiber introduces a change in the spacing of this grating and, hence, of the wavelength of light reflected back up the fiber. This wavelength shift is measured to determine the amount of strain in the grating portion of the fiber. In addition to our work [13, 14], others have applied FBG force sensors to other sorts of surgical instrumentation. For example Mueller et al. [22] have reported a 6-DOF FBG-based force/torque sensor based on FBG sensors that would be suitable for mounting in the tool handle or proximal end of robotic surgical instruments, in a manner somewhat analogous to [9].

Optical fiber-based sensors have many advantages for microsurgical applications. The fibers and sensors are inexpensive. They are sterilizable by a variety of common means. They can be made biocompatible. They can be made very small. They are immune to electrical noise and magnetic fields. They involve no electrical currents. A number of sensing principles may be used to measure delicate displacements and forces. Further, although this is not a consideration for retinal surgery, they are MRI compatible.

In previously published work [13, 14], our JHU team has incorporated FBG fibers into the tool shafts of 0.5-0.7 mm microsurgical instruments to make 1-DOF and 2-DOF force sensing tools with force resolutions on the order of 0.25 mN. Our team has also developed 3-DOF FBG based microsurgical instruments. One concept for a 3-DOF force sensing tool is shown in FIG. 2A. Here, lateral forces are measured by FBG sensors; just as in our 2-DOF tools, and axial forces are measured by a force sensor in the handle. The advantage of this scheme is simplicity. However, one major drawback is that, although ambiguities introduced by lateral sclera-tool interactions are eliminated, axial ambiguities introduced by sclera-to-tool friction are not.

This consideration has led us to develop prototype 3-DOF tools with all sensing inside the eye [26], as shown in FIG. 2B. In this design, FBG sensors along the sides of the shaft measure lateral deflections of the tool shaft as a result of lateral forces, much as is the case with our 2-DOF tools. In principle, the axial extension of the tool shaft in response to axial forces could also be measured, but there are several drawbacks. First, the tool is very stiff in the axial direction, resulting in low sensitivity. Second, thermal expansion of the tool can also stretch all the fibers. Consequently, lateral forces are actually computed differentially, using 3 FBG sensors to compute two lateral forces. For axial forces, we use a fourth FBG fiber running axially through the middle of the tool and attached to the distal end of a micro-machined compliant section of the tool shaft.

There are, however, a number of problems with microsurgical sensors based on FBG sensing, which our current invention seeks to address. Some of these problems include:

The FBG fibers must be firmly attached along the sides of the tool. This can involve a difficult manufacturing process, and glue compliance, viscous response, and hysteresis between the FBG and the tool shaft can introduce problems. There are similar (and even more challenging) manufacturing and attachment problems associated with the "axial" fiber, which must also be pre-loaded.

The FBG fibers have significant stiffness. This especially affects the axial force sensitivity of the tool, since the mechanical advantage from the bending of the tool shaft on the stretching of the lateral FBG fibers is lost.

The micro-machined grooves into the tool shaft to produce a compliant section, as shown in FIG. 2B, can become clogged with material, thus affecting the tool's calibration and also creating cleaning/sterilization problems if the tool is to be reused.

Obtaining good signal-to-noise characteristics requires that the FBG grating be fairly long (typically about 10 mm on our microsurgical tools). This constrains the design of the tool and also can cause problems if external forces are exerted on that portion of the tool shaft containing or proximal to the grating.

There thus remains a need for improved surgical tools and systems for microsurgical applications.

SUMMARY

A surgical tool system according to an embodiment of the current invention includes a surgical tool, and an interferometry system optically coupled to the surgical tool. The surgical tool includes a body section, a sensor section at least one of attached to or integral with the body section, and a surgical section at least one of attached to or integral with the sensor section at an opposing end of the sensor section from the body section. The sensor section comprises an interferometric optical sensor defining a reference distance that changes in response to at least one of a force or a torque when applied to the surgical section of the surgical tool.

A surgical tool according to an embodiment of the current invention includes a body section, a sensor section at least one of attached to or integral with the body section, and a surgical section at least one of attached to or integral with the sensor section at an opposing end of the sensor section from the body section. The sensor section includes an interferometric optical sensor defining a reference distance that changes in response to at least one of a force or a torque applied to the surgical section of the surgical tool.

BRIEF DESCRIPTION OF THE DRAWINGS

Further objectives and advantages will become apparent from a consideration of the description, drawings, and examples.

FIG. 2A shows lateral forces from FBG sensors on the tool shaft and an axial force sensor in the handle. FIG. 2B shows lateral forces from FBG sensors measuring lateral deflections of the tool shaft and axial forces from additional fiber measuring extension of a micro-machined compliant section of the shaft.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Although FBG sensors are relatively easy to use and have been employed by several groups (including ours) for surgical force measurement, they do have some significant disadvantages, especially in, but not limited to, microsurgical environments.

A fiber Bragg grating reflects a narrow wavelength band of light that depends on the spacing of the periodic pattern of varying refractive index. (The term "light" as used herein is meant to have a broad meaning that can include, visible, infrared and ultraviolet light, for example.) A number of other phase-modulated or interferometric sensor types are known [5, 20]. One such type is the Fabry-Perot interferometer. The general concept of a phase-modulated sensor is that the sensor employs two fibers. The light is split into two arms and injected into each arm. One arm works as a reference while the other can be perturbed by the environment. When one arm is perturbed relative to the reference fiber, the change in interference fringes such as the phase shift can be measured precisely by the interferometer. The Fabry-Perot interferometer requires only one fiber. The light beam is reflected by a separate reflector and then interferes with the reference that is derived from the fiber tip [5, 20]. The configuration can be either intrinsic or extrinsic, as shown in FIG. 3.

Figure 3:
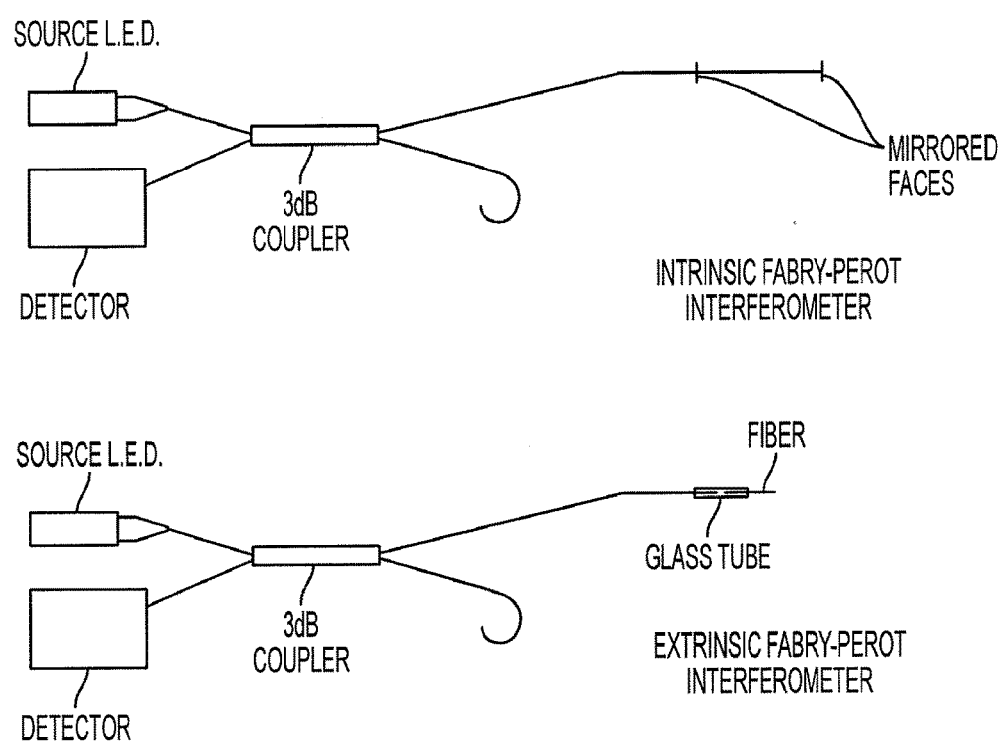
FIG. 3 illustrates concepts of intrinsic and extrinsic Fabry-Perot interferometers [5] for use with some embodiments of the current invention.
Figure 4:
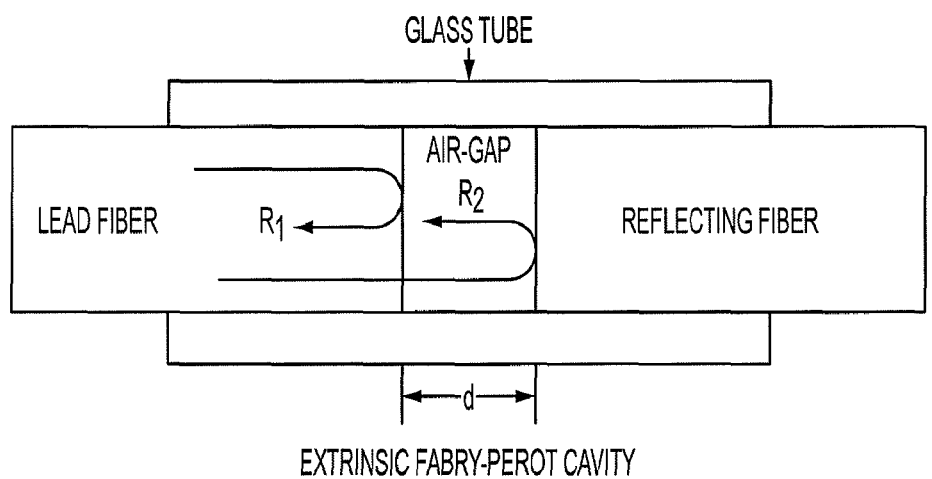
FIG. 4 is a more detailed view of a typical extrinsic Fabry-Perot sensor [27] corresponding to the lower portion of FIG. 3.

FIG. 4 shows a close-up view of a typical extrinsic configuration corresponding to the lower diagram in FIG. 3. With the air gap between the lead fiber and reflecting fiber, two reflection surfaces are formed, the first reflecting surface at the end of the lead fiber and the second reflecting surface at the reflecting fiber face. The light beam is partially reflected at the first surface and partially transmitted into the air gap. This happens again for the transmitted beam at the second surface (the second reflecting surface could be either partial or totally reflecting). The light beam at the second reflecting surface is then at least partially reflected back and re-enters the lead fiber. The second reflection travels a longer distance (twice the air gap length) than light from the first reflection [27], [5].

Therefore, some embodiments of the current invention make use of forms of interferometric sensing other than FBG sensing to measure small geometric changes in the microsurgical instrument as it complies to tool-to-tissue forces. The term interferometric sensor is intended to exclude FBG devices which are essentially wavelength selective reflectors rather than devices that mix two light beams to determine an optical phase difference.

Figure 5:
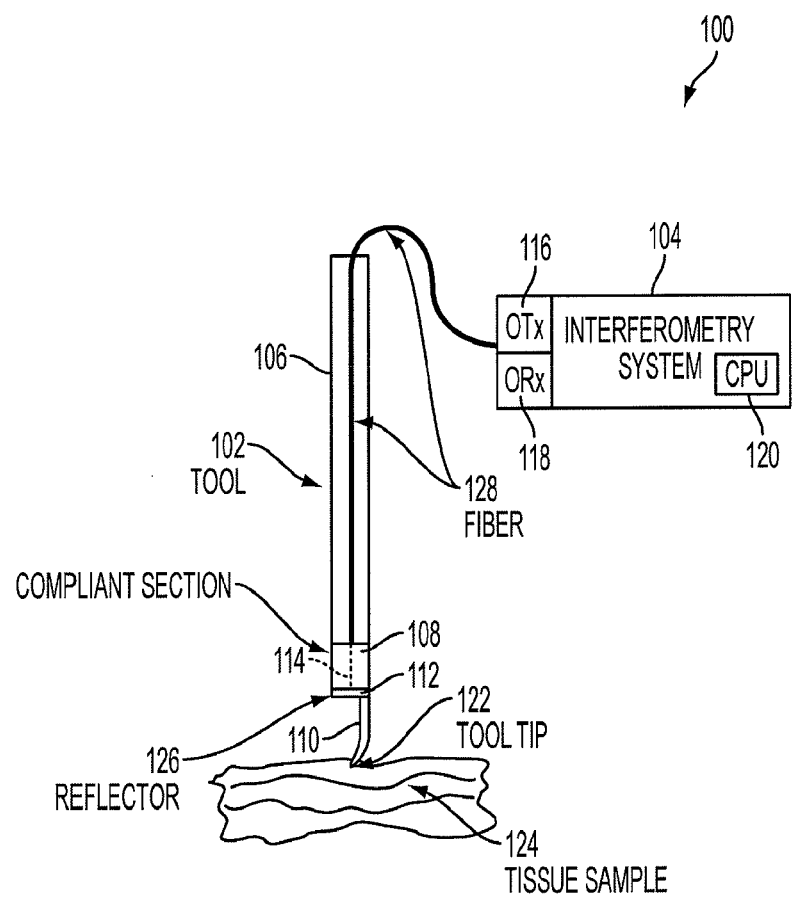
FIG. 5 is a schematic illustration of a surgical tool and surgical tool system according to an embodiment of the current invention.

FIG. 5 is a schematic illustration of a surgical tool system 100 according to an embodiment of the current invention. The surgical tool system 100 includes a surgical tool 102, and an interferometry system 104 optically coupled to the surgical tool 102. The surgical tool 102 includes a body section 106, a sensor section 108 at least one of attached to or integral with the body section 106, and a surgical section 110 at least one of attached to or integral with the sensor section 108 at an opposing end 112 of the sensor section 108 from said body section 106. The sensor section 108 includes an interferometric optical sensor defining a reference distance 114 that changes in response to at least one of a force or a torque when applied to the surgical section 108 of the surgical tool 102.

The interferometry system 104 includes an optical transmitter 116 arranged to transmit light to the interferometric optical sensor, an optical receiver 118 arranged to detect light returned from the interferometric optical sensor such that it provides an output signal, and a signal processor 120 constructed to communicate with the optical receiver 118 to receive the output signal. The optical transmitter 116, optical receiver 118 and signal processor 120 can be packaged together, or can be separate individual and/or distributed components. The signal processor can be a dedicated, "hardwired" device and/or a programmable device, such as, but not limited to a computer. The signal processor 120 is configured to determine a change in the reference distance 114 of the interferometric optical sensor from the output signal from the optical receiver 118 and to determine at least one of an applied force, an applied torque or a local temperature change. In an embodiment, the signal processor 120 can be configured to determine a change in the reference distance 114 of the interferometric optical sensor 108 from the output signal from the optical receiver 118 and use it to determine an applied force on the tool tip 122 of the surgical section 110 with the tissue 124 taking into account a local temperature change.

The interferometric optical sensor in sensor section 108 is an intrinsic type Fabry-Perot sensor, such as described in the top of FIG. 3. The reference distance 114 of the interferometric optical sensor is defined by two opposing surfaces of a solid material. Each of the two opposing surfaces is at least a partially reflecting surface. If desired, the reflecting surface 126 can be totally reflecting while the opposing reflecting surface is partially reflecting due to an interface of two materials with different refractive indices. The solid material sensor section 108 is a compliant solid material that can be compressed and elongated in response to varying forces applied to the surgical section 110 to provide a change in the reference distance 114.

The surgical tool system 100 further includes an optical fiber 128 extending along an internal portion of the body section 106 to the sensor section 108 of the surgical tool 102.

In some embodiments, the surgical tool 102 can be, but is not limited to, a micro-surgical tool. In some embodiments, the micro-surgical tool can be, but is not limited to, a needle, a pick, a scalpel, forceps, scissors, or a trocar.

Figure 6:
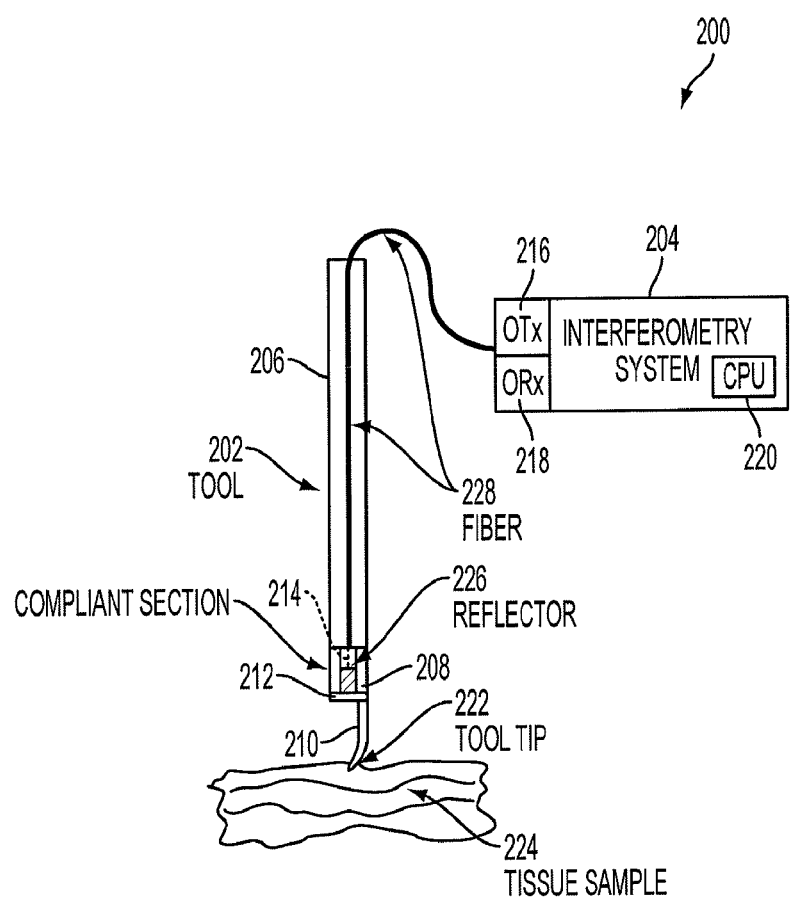
FIG. 6 is a schematic illustration of a surgical tool and surgical tool system according to another embodiment of the current invention.

FIG. 6 is a schematic illustration of a surgical tool system 200 according to an embodiment of the current invention. The surgical tool system 200 includes a surgical tool 202, and an interferometry system 204 optically coupled to the surgical tool 202. The surgical tool 202 includes a body section 206, a sensor section 208 at least one of attached to or integral with the body section 206, and a surgical section 210 at least one of attached to or integral with the sensor section 208 at an opposing end 212 of the sensor section 208 from said body section 206. The sensor section 208 includes an interferometric optical sensor defining a reference distance 214 that changes in response to at least one of a force or a torque when applied to the surgical section 208 of the surgical tool 202.

The interferometry system 204 includes an optical transmitter 216 arranged to transmit light to the interferometric optical sensor, an optical receiver 218 arranged to detect light returned from the interferometric optical sensor such that it provides an output signal, and a signal processor 220 constructed to communicate with the optical receiver 218 to receive the output signal. The optical transmitter 216, optical receiver 218 and signal processor 220 can be packaged together, or can be separate individual and/or distributed components. The signal processor can be a dedicated, "hardwired" device and/or a programmable device, such as, but not limited to a computer. The signal processor 220 is configured to determine a change in the reference distance 214 of the interferometric optical sensor from the output signal from the optical receiver 218 and to determine at least one of an applied force, an applied torque or a local temperature change. In an embodiment, the signal processor 220 can be configured to determine a change in the reference distance 214 of the interferometric optical sensor 208 from the output signal from the optical receiver 218 and use it to determine an applied force on the tool tip 222 of the surgical section 210 with the tissue 224 taking into account a local temperature change.

The interferometric optical sensor in sensor section 208 is an extrinsic type Fabry-Perot sensor, such as described in the bottom of FIG. 3 and FIG. 4. The reference distance 214 of the interferometric optical sensor is defined by two opposing surfaces of a gap. Each of the two opposing surfaces is at least a partially reflecting surface. If desired, the reflecting surface 226 can be totally reflecting while the opposing reflecting surface is partially reflecting due to an interface of two materials with different refractive indices. The sensor section 208 can include a compliant material or structure that can be compressed and elongated in response to varying forces applied to the surgical section 210 to provide a change in the reference distance 214. For example, the sensor section 208 can include, but is not limited to, a cylindrical elastic material, or a micromachined cylindrical section.

The surgical tool system 200 further includes an optical fiber 228 extending along an internal portion of the body section 206 to the sensor section 208 of the surgical tool 202.

In some embodiments, the surgical tool 202 can be, but is not limited to, a micro-surgical tool. In some embodiments, the micro-surgical tool can be, but is not limited to, a needle, a pick, a scalpel, forceps, scissors, or a trocar.

Figure 7A:
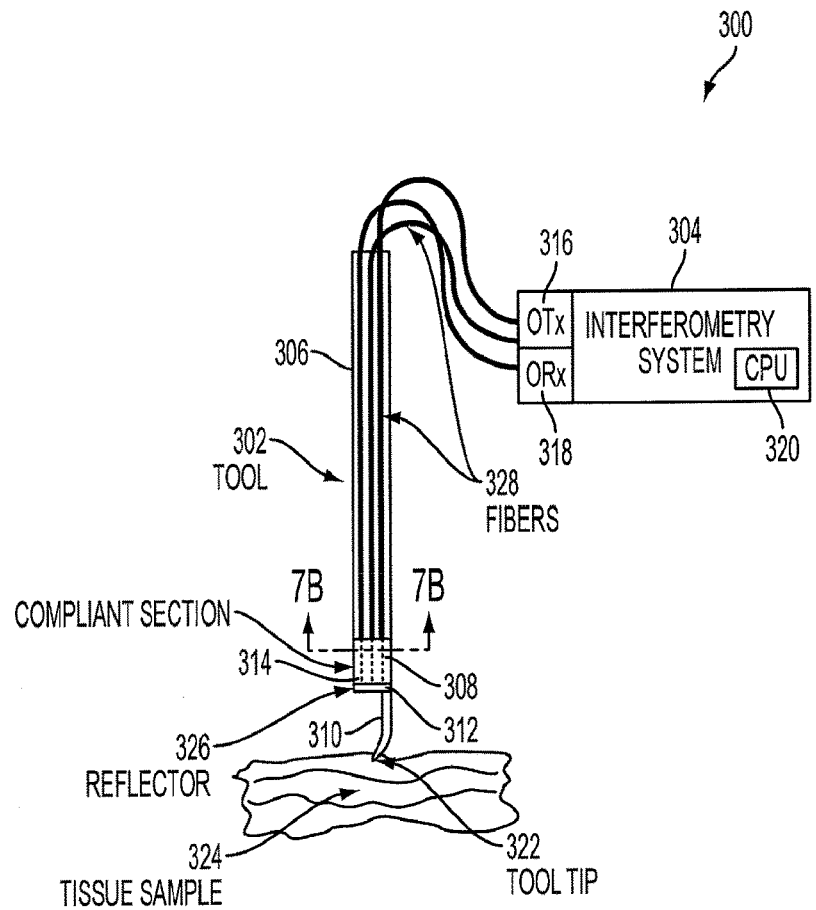
FIGS. 7A and 7B are schematic illustrations of a surgical tool and surgical tool system according to another embodiment of the current invention.
Figure 7B:
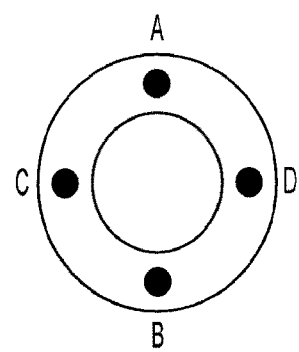

FIG. 7A is a schematic illustration of a surgical tool system 300 according to another embodiment of the current invention. The surgical tool system 300 includes a surgical tool 302, and an interferometry system 304 optically coupled to the surgical tool 302. The surgical tool 302 includes a body section 306, a sensor section 308 at least one of attached to or integral with the body section 306, and a surgical section 310 at least one of attached to or integral with the sensor section 308 at an opposing end 312 of the sensor section 308 from said body section 306. The sensor section 308 includes a plurality of interferometric optical sensors defining corresponding reference distances 314 that change in response to at least one of a force or a torque when applied to the surgical section 308 of the surgical tool 302. (See, also, FIG. 7B corresponding to the cut line indicated in FIG. 7A.) In this example, there are four Fabry-Perot interferometers arranged circumferentially. However, the concepts of the current invention are not limited to the particular number and arrangement of the interferometers. There could be one, two, three or four interferometers, or even more according to some embodiments. They could also be arranged in various patterns, such as, but not limited to, one centrally, and none, one, two, three or more arranged circumferentially, for example. However, other arrangements of interferometers can be used according to other embodiments of the current invention.

The interferometry system 304 includes an optical transmitter 316 arranged to transmit light to the plurality of interferometric optical sensors, an optical receiver 318 arranged to detect light returned from the plurality of interferometric optical sensors such that it provides an output signal, and a signal processor 320 constructed to communicate with the optical receiver 318 to receive the output signal. The optical transmitter 316, optical receiver 318 and signal processor 320 can be packaged together, or can be separate individual and/or distributed components. The signal processor can be a dedicated, "hard-wired" device and/or a programmable device, such as, but not limited to a computer. The signal processor 320 is configured to determine a change in the reference distances 314 of the plurality of interferometric optical sensors from the output signal from the optical receiver 318 and to determine at least one of an applied force, an applied torque or a local temperature change. In an embodiment, the signal processor 320 can be configured to determine a change in the reference distances 314 of the interferometric optical sensors from the output signal from the optical receiver 318 and use it to determine an applied force on the tool tip 322 of the surgical section 310 with the tissue 324 taking into account a local temperature change.

The interferometric optical sensors in sensor section 308 are intrinsic type Fabry-Perot sensors, such as described in the top of FIG. 3. However, one or more could be constructed as extrinsic Fabry-Perot sensors. These sensors can be constructed similar to the intrinsic and extrinsic Fabry-Perot sensors described with respect to the above embodiments, for example.

The surgical tool system 300 further includes a plurality of optical fibers 328 extending along an internal portion of the body section 306 to the sensor section 308 of the surgical tool 302.

In some embodiments, the surgical tool 302 can be, but is not limited to, a micro-surgical tool. In some embodiments, the micro-surgical tool can be, but is not limited to, a needle, a pick, a scalpel, forceps, scissors, or a trocar.

Figure 8A:
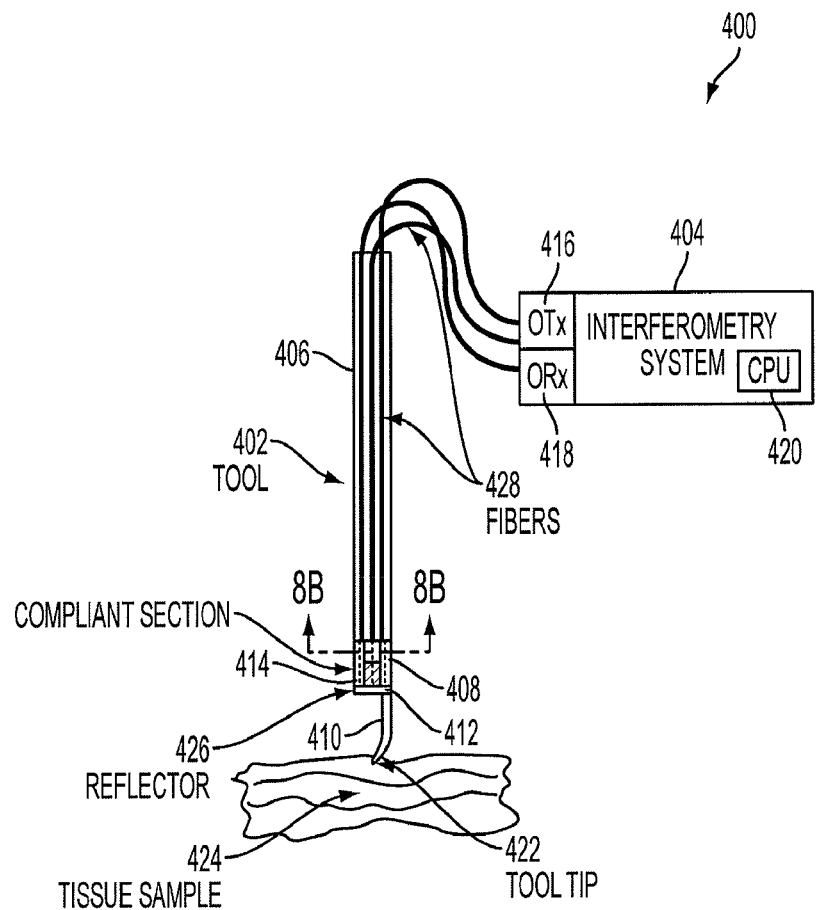
FIGS. 8A and 8B are schematic illustrations of a surgical tool and surgical tool system according to another embodiment of the current invention.
Figure 8B:
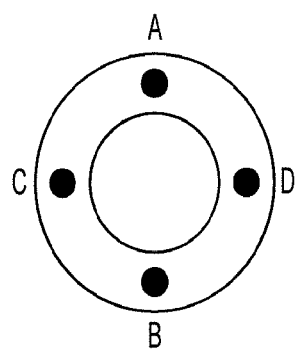

FIG. 8A is a schematic illustration of a surgical tool system 400 according to another embodiment of the current invention. The surgical tool system 400 includes a surgical tool 402, and an interferometry system 404 optically coupled to the surgical tool 402. The surgical tool 402 includes a body section 406, a sensor section 408 at least one of attached to or integral with the body section 406, and a surgical section 410 at least one of attached to or integral with the sensor section 408 at an opposing end 412 of the sensor section 408 from said body section 406. The sensor section 408 includes a plurality of interferometric optical sensors defining corresponding reference distances 414 that change in response to at least one of a force or a torque when applied to the surgical section 408 of the surgical tool 402. (See, also, FIG. 8B corresponding to the cut line indicated in FIG. 8A.) In this example, there are four Fabry-Perot interferometers arranged circumferentially. However, the concepts of the current invention are not limited to the particular number and arrangement of the interferometers. There could be one, two, three or four interferometers, or even more according to some embodiments. They could also be arranged in various patterns, such as, but not limited to, one centrally, and none, one, two, three or more arranged circumferentially, for example. However, other arrangements of interferometers can be used according to other embodiments of the current invention.

The interferometry system 404 includes an optical transmitter 416 arranged to transmit light to the plurality of interferometric optical sensors, an optical receiver 418 arranged to detect light returned from the plurality of interferometric optical sensors such that it provides an output signal, and a signal processor 420 constructed to communicate with the optical receiver 418 to receive the output signal. The optical transmitter 416, optical receiver 418 and signal processor 420 can be packaged together, or can be separate individual and/or distributed components. The signal processor can be a dedicated, "hard-wired" device and/or a programmable device, such as, but not limited to a computer. The signal processor 420 is configured to determine a change in the reference distances 414 of the plurality of interferometric optical sensors from the output signal from the optical receiver 418 and to determine at least one of an applied force, an applied torque or a local temperature change. In an embodiment, the signal processor 420 can be configured to determine a change in the reference distances 414 of the interferometric optical sensors from the output signal from the optical receiver 418 and use it to determine an applied force on the tool tip 422 of the surgical section 410 with the tissue 424 taking into account a local temperature change.

The interferometric optical sensors in sensor section 308 are intrinsic type Fabry-Perot sensors, such as described in the top of FIG. 3. However, one or more could be constructed as intrinsic Fabry-Perot sensors. These sensors can be constructed similar to the intrinsic and extrinsic Fabry-Perot sensors described with respect to the above embodiments, for example.

The surgical tool system 400 further includes a plurality of optical fibers 428 extending along an internal portion of the body section 306 to the sensor section 408 of the surgical tool 402.

In some embodiments, the surgical tool 402 can be, but is not limited to, a micro-surgical tool. In some embodiments, the micro-surgical tool can be, but is not limited to, a needle, a pick, a scalpel, forceps, scissors, or a trocar.

Sensor sections according to various embodiments of the current invention can include a compliant component that is a micro-machined tube comprising flexures, for example. In some embodiments, the micro-machined tube may consist of Nitinol material, although other elastic materials may be substituted, depending on the desired stiffness and other operational properties for the intended application". Examples include, but are not limited to steel and titanium. In some embodiments, the sensor section can further include a compliant sealing material disposed in gaps between the flexures of the micro-machined tube. The compliant section can include a material that is substantially transparent to an operating wavelength of the interferometric optical sensor. Sensor section according to some embodiments of the current invention can further include a flexible membrane attached around the compliant section to provide a shield.

We can now illustrate some concepts with a simple 1-DOF axial force sensing tool, shown in FIGS. 5 and 6. In this example, a small compliant section is placed on the distal portion of the tool shaft, proximal to the portion of the tool tip that may experience any tool-tissue interaction forces. For simplicity, we will assume that the compliant section only complies to forces exerted on the tool tip in a direction parallel to the tool shaft axis. Any one of a number of known structures may be used to provide the compliant section. For example:

A flexure structure may be etched or machined into the end of the microsurgical tool shaft.

A separate compliant material (different from that of the tool shaft) may be fabricated and attached to the end of the tool shaft. One example of such a material might be a polymeric material.

Figure 1:
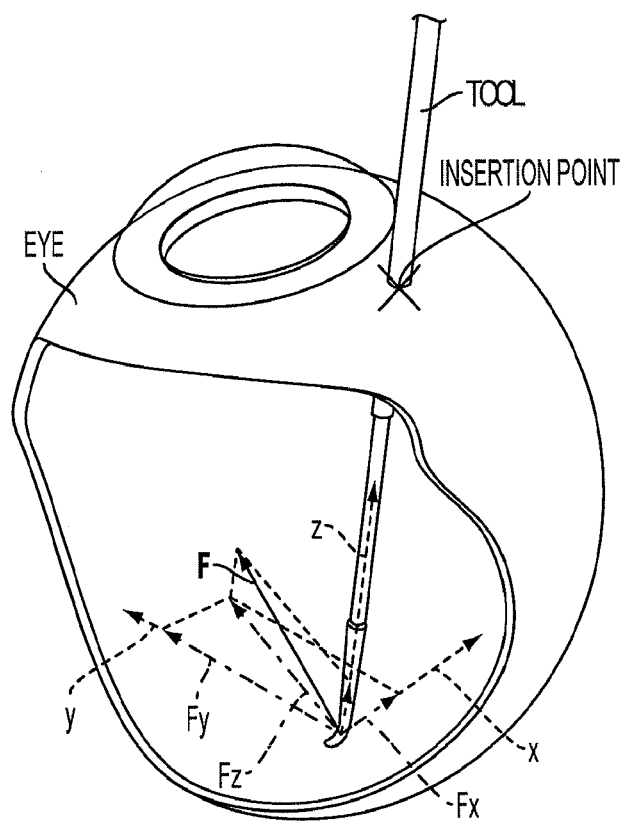
FIG. 1 illustrates a microsurgical tool and forces that can occur in retinal surgery [13, 14] to help explain some concepts of the current invention.
Figure 2B:
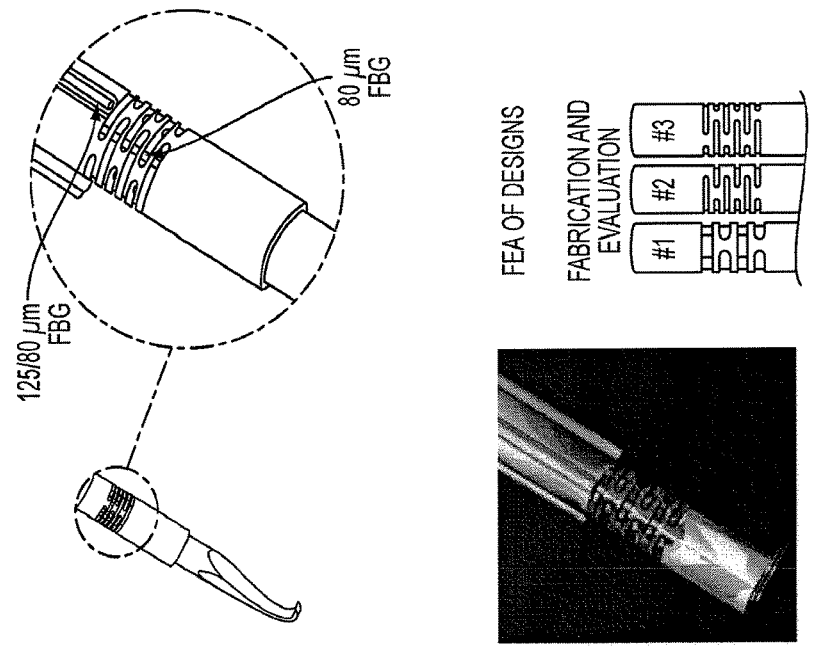
FIGS. 2A and 2B illustrate FBG-based 3DOF force sensing tool concepts.
Figure 2A:
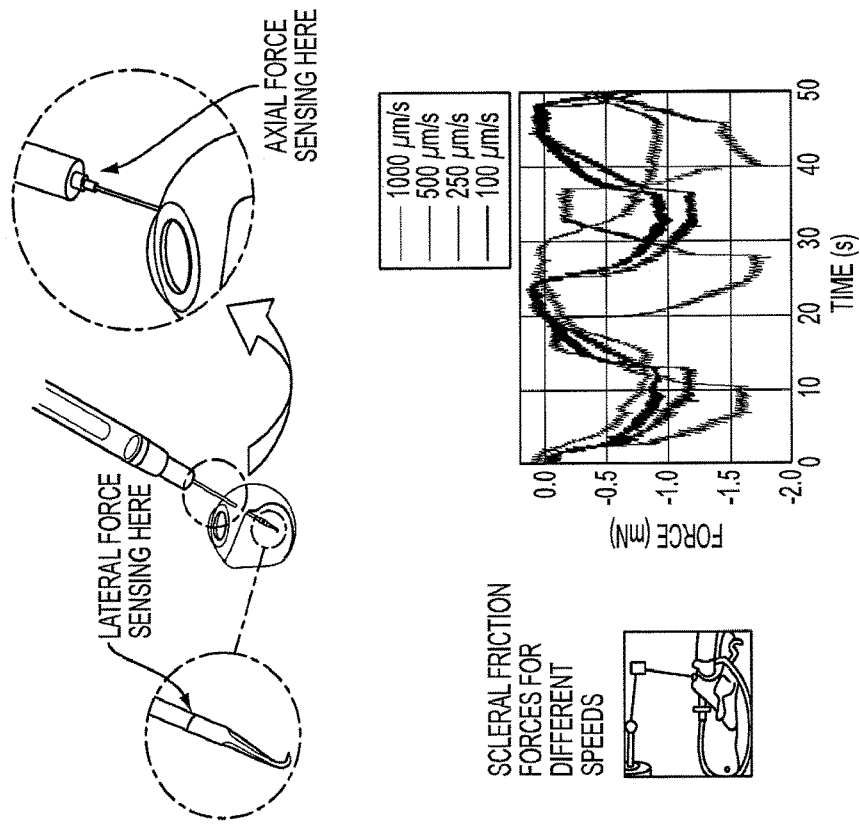

An optical fiber is passed down the tool shaft, so that light passing through the fiber bounces off a reflecting surface that moves with the tool tip portion of the tool (i.e., that portion distal to the compliant section) and back into the fiber. In some applications, it may be necessary to provide an additional reference reflecting surface on the distal end of the fiber, using standard means know in the art. The compliant section is so constructed that light can pass from the fiber to the reflecting surface and back again. This may easily be accomplished if the compliant section has the general form of a tube, so that there is a clear path between the fiber and the reflecting surface. For example, the machined flexure structure of FIG. 2B has this form. Alternatively, the compliant structure may be made of some transparent solid material with consistent elastic properties. If the index of refraction of this material is not different from the material in the fiber, then a semi-reflecting mirror needs to be added to the end of the fiber. In yet another embodiment, it may be desirable to "fill" a flexure-style compliant structure such as that in FIG. 2B with a low stiffness, transparent compliant material to exclude contamination. Alternatively, the compliant structure may be covered with an appropriate flexible sheath to accomplish the purpose of preventing contamination.

Any interferometric method known in the art [5, 20] may be used to measure the change Dz in axial displacement of the reflecting surface in response to a force change $Df_z$ in the axial force exerted on the tool. In one embodiment, Fabry-Perot interferometry [5, 20, 27] may be used. In another embodiment, a common-path optical coherence tomography (CPOCT) system [28-30] may be used. In both cases, to achieve high sensitivity, phase sensitive measurement needs to be employed. The phase of the Fabry-Perot interferometer can be extracted from the interferogram using:

$$\phi = \arctan\left(\frac{\operatorname{Im}(F(\text{interferomgram}))}{\operatorname{Re}(F(\text{interferomgram}))}\right) = \frac{4\pi}{\lambda_0}\Delta z$$

thus giving another accurate method for computing Dz.

Any convenient calibration method known in the art may be used to determine the compliance $C_z$ relating $\Delta z$ and $\Delta f_z$, so that the relation $\Delta f_z = C_z \Delta z$ may be used to determine $\Delta f_z$ from a measured value $\Delta z$ with high sensitivity. Assuming this simple model, the distance $z = z_0 + \Delta z$ corresponds to a force $f_z = f_{z0} + \Delta f_z = C_z \times (z_0 + \Delta z)$. It is customary to "re-bias" the force sensor in common use by measuring the displacement $z_0$ corresponding to some "zero" force $f_{z0} = 0$, and then subtracting $z_0$ from the measured value of z, i.e., we take $\Delta z = z_{meas} - z_0$ and $f_z = C_z \Delta z$.

This basic design may be extended to provide sensing of multiple degrees-of-freedom forces and torques. Consider the tool designs shown in FIGS. 7A and 8A. In this case, a compliant tool section is placed between the proximal tool shaft and the distal portion of the tool that contacts tissue. Multiple fibers are passed along the proximal tool shaft and arranged so that light can pass from the fibers to reflective surfaces that move with the distal portion of the tool, so that light is reflected back up the fibers into the interferometry system. One typical arrangement of fibers is shown in FIGS. 7A and 8A.

For convenience, let $\vec{f} = [t_1, L\, t_m]^T$ be a vector of forces and torques resolved at a known point on the distal portion of the tool. Let $D\vec{z} = [z_1, L, z_d]^T$ be a vector of measured displacements of the reflecting surface from some assumed "zero" torque position, typically measured as a result of a "re-biasing" step. Then we have the compliance relation $D\vec{z} = K_{d\vec{r}m}\vec{f}$ and $\vec{f} = c_{m\vec{r}d}D\vec{z}$, where $C = K^+$ is an appropriate pseudo-inverse of K. For example, suppose that the tool tip is located at coordinates $[0, 0, 0]^T$, that the reflecting surface is perpendicular to the tool shaft ($\vec{z}$) axis, and that there are four fibers arranged so that the reflecting points are at $\vec{x}_A = [0, r, h]$ $\vec{x}_B = [0, -r, h]$ $\vec{x}_C = [-r, 0, h]$ $\vec{x}_D = [r, 0, h]$ Suppose that we assume that only Cartesian forces (no torques) are exerted at the tool tip. Then, to a first approximation sufficiently accurate for small displacements we might have, in an idealized situation, $$\begin{bmatrix} \Delta z_A \\ \Delta z_B \\ \Delta z_C \\ \Delta z_D \end{bmatrix} \approx \begin{bmatrix} 0 & rk_y/h & k_z \\ 0 & -rk_y/h & k_z \\ -rk_x/h & 0 & k_z \\ rk_x/h & 0 & k_z \end{bmatrix} \begin{bmatrix} f_x \\ f_y \\ f_z \end{bmatrix}$$

where $k_x$, $k_y$, $k_z$ are effective spring constants. After suitable calibration, we can determine these coefficients and compute a C. As a practical matter, most calibration methods will exert a number of known forces $\vec{f}^{(k)}$ and measure the corresponding displacement vectors $\vec{z}^{(k)}$ and then estimate C numerically. Note that the above formulas are intended for illustration only. There is no specific requirement on the elements of the matrix K, other than that the elements be consistent and that the pseudo-inverse $C = K^+$ be computable. Different compliant structures will produce different matrices.

We note that although this example assumes that the optical fibers and light paths to the reflectors are arranged to run parallel to the tool shaft, this is not at all required. Depending on the design requirements of specific tools they may be arranged to run at any arbitrary directions and have any arbitrary displacements relative to the tool. As a general proposition, the tool should be designed so that systems $\vec{f} = C_{m \times d} \Delta \vec{z}$ and $\Delta \vec{z} = K_{d \times m} \vec{f}$ are numerically well conditioned and that any of the desired forces and torques produce significant measurements of the corresponding $\Delta \vec{z}$.

So far, this discussion has ignored the effect of thermal expansion of the surgical instrument. In general, a temperature change $\Delta T$ in the compliant section of the tool can cause a change in the measured values of the $\Delta z_j$, $$\Delta \vec{z} = K_{comply} \vec{f} + K_{temp} \Delta T$$

where we can usually approximate $$K_{temp} \approx \begin{bmatrix} k_{temp,1} & & & \\ & 0 & & \\ & & k_{temp,i} & \\ & & & 0 \\ & & & & k_{temp,d} \end{bmatrix}$$

In many circumstances (for instance if $\Delta T$ is very small or if $|K_{temp} \Delta T| \ll |K_{comply} \vec{f}|$ over the time period that measurements are needed) the temperature effects may be ignored. Alternatively, suitable calibration procedures may be used to estimate $K_{comply}$ and $K_{temp}$, provided that there is sufficient redundancy in the sensing system and compliant structure design to separate changes in $\Delta z$ due to temperature changes and changes due to forces to be measured.

Figure 9C:
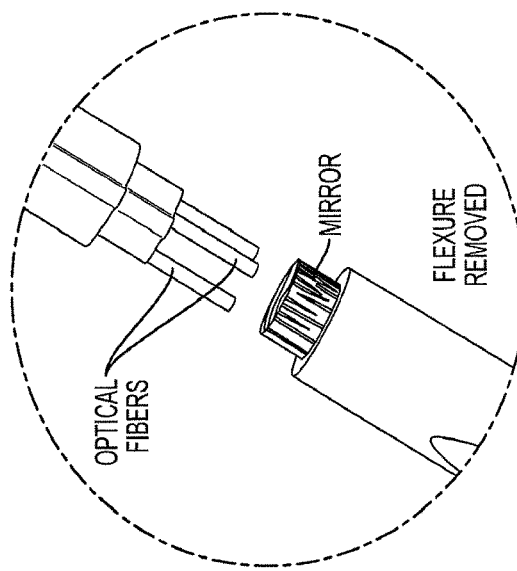
FIGS. 9A-9C are illustrations of a surgical tool including an example with a Nitinol flexure according to an embodiment of the current invention.
Figure 9B:
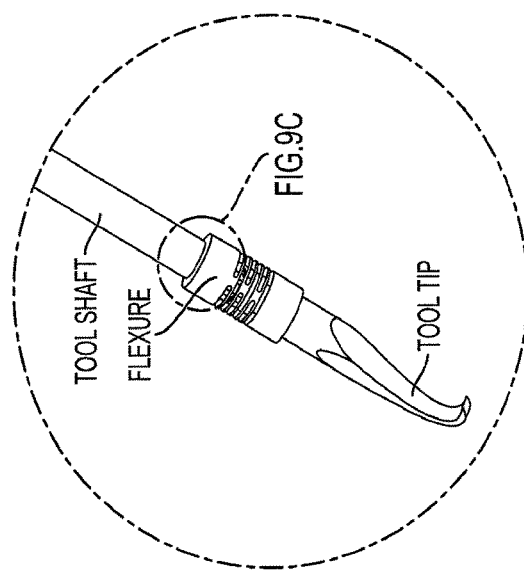
Figure 9A:
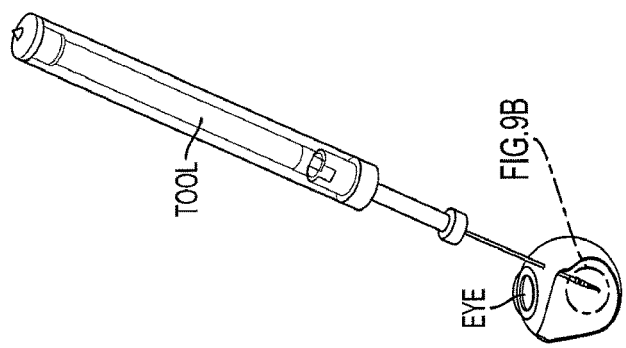
Figure 10:
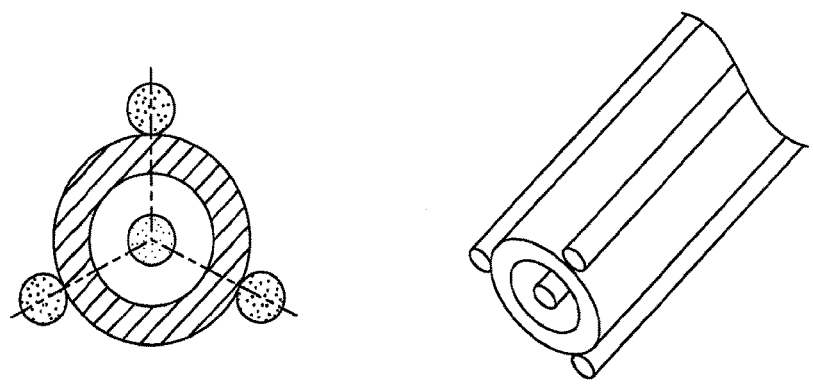
FIG. 10 illustrates an alternative arrangement of optical sensing fibers according to another embodiment of the current invention.

FIGS. 9A-9C show further details of a 3-DOF FP force sensor similar to that described above. In this case, three optical fibers placed at 120 degree angles about the tool shaft are provided, thus providing a minimal configuration for sensing three force components. If desired, a fourth fiber sensor may easily be provided as shown in FIGS. 7A and 8A in order to provide redundancy or temperature compensation. Or the illustrated arrangement of 3 fibers around the sides of the tool could be supplemented with a fourth fiber running down the middle of the tool, as shown in FIG. 10. Alternatively, this 3-fiber configuration may be used to sense only lateral forces, with temperature compensation.

Figure 11:
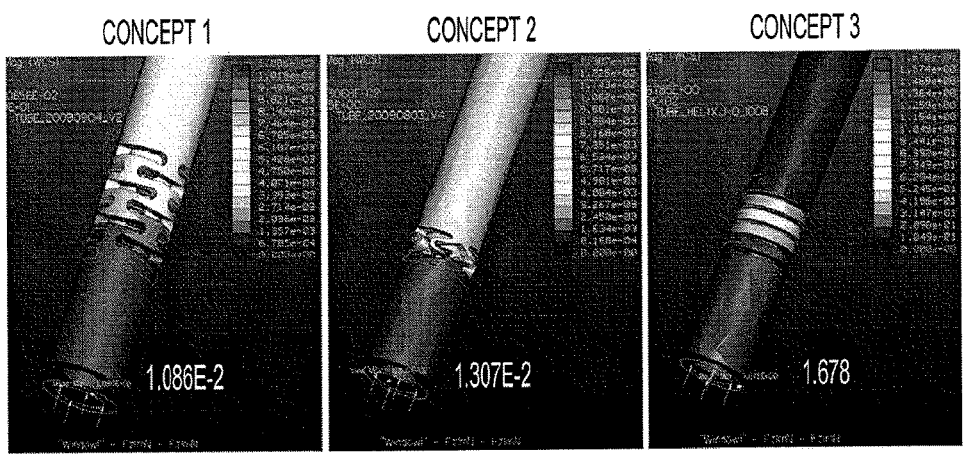
FIG. 11 illustrates some concepts of compliant sections using examples of machined Nitinol tubes according to embodiments of the current invention. Deflections under 1 mN axial deflection are shown.

In this case, the compliant section is constructed from a micro-machined Nitinol (nickel-titanium alloy) tube. FIG. 11 shows several concepts with finite element simulations of deflections under 1 mN axial force.

Figure 12:
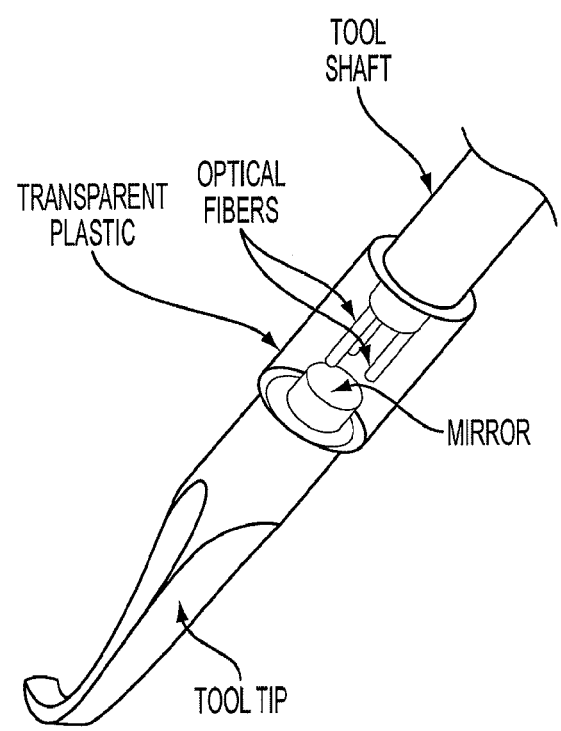
FIG. 12 shows an example of 3-DOF force sensing tool with plastic compliant section according to an embodiment of the current invention.

FIG. 12 shows an alternative solution where the metal flexure is replaced with a cylinder made by transparent plastic with consistent elastic properties. Advantages of this concept include: simplicity and low cost; easier cleaning; strength and robustness.

In other embodiments, there is no requirement that all optical fibers use the same sensing method. For example, in the arrangement of fibers is as in FIG. 10, the lateral fibers could be FBG sensors attached to the sides of the shaft and the central fiber could be a Fabry-Perot sensor looking at a mirror at the distal end of an axially compliant section between the tool shaft and tool tip. The FBG sensors could be used to measure lateral forces, which bend the shaft, and the Fabry-Perot sensor could be used to measure axial forces compressing the axially compliant section.

Surgical tools and surgical tool systems according to some embodiments of the current invention can be used to provide feedback to the surgeon by, for example, haptic, visual and/or audio feedback.

REFERENCES

[1] P. Gupta, P. Jensen, and E. deJuan, "Surgical Forces and Tactile Perception During Retinal Microsurgery", in *Proceedings of the Second International Conference on Medical Image Computing and Computer-Assisted Intervention (MICCAI 99)*, Cambridge, England, 1999, pp. 1218-1225

[2] P. Jensen, P. Gupta, and J. E. de Juan, "Quantification of microsurgical tactile perception", in *The First Joint Meeting of BMES and EMBS*, Atlanta, 1999

[3] P. K. Gupta, *A Method to Enhance Microsurgical Tactile Perception and Performance Through the Use of Auditory Sensory Perception*, thesis in M.S. in Engineering, The Johns Hopkins University, Baltimore, 2001.

[4] A. D. Jagtap and C. N. Riviere, "Applied Force during Vitreoretinal Microsurgery with Handheld Instruments", in *Proc. 26th IEEE Engineering in Medicine and Biology Conference (EMBS)*, San Francisco, 2004, pp. 2771-2773

[5] D. A. Krohn, *Fiber Optic Sensors: Fundamentals and Applications*: Instrument Society of America, 2000.

[6] P. J. Berkelman, D. L. Rothbaum, J. Roy, Sam Lang, L. L. Whitcomb, G. Hager, P. S. Jensen, R. H. Taylor, and J. Niparko, "Performance Evaluation of a Cooperative Manipulation Microsurgical Assistant Robot Applied to Stapedotomy", in *Medical Image Computing and Computer-Assisted Interventions (MICCAI 2001)*, Utrecht, 2001, pp. 1426-1429

[7] D. L. Rothbaum, J. Roy, P. Berkelman, G. Hager, D. Stoianovici, R. H. Taylor, L. L. Whitcomb, M. Howard Francis, and J. K. Niparko, "Robot-assisted stapedotomy: micropick fenestration of the stapes footplate", *Otolaryngology—Head and Neck Surgery*, vol. 127-5, pp. 417-426, November 2002

[8] D. Rothbaum, J. Roy, G. Hager, R. Taylor, and L. Whitcomb, "Task Performance in stapedotomy: Comparison between surgeons of different experience levels", *Otolaryngology—Head and Neck Surgery*, vol. 128-1, pp. 71-77, January 2003

[9] P. J. Berkelman, L. Whitcomb, R. Taylor, and P. Jensen, "A miniature microsurgical instrument tip force sensor for enhanced force feedback during robot-assisted manipulation", *IEEE T. Robotics and Automation*, vol. 19-5, pp. 917-922, October 2003

[10] M. Balicki, A. Uneri, I. Iordachita, J. Handa, P. Gehlbach, and R. H. Taylor, "Micro-force Sensing in Robot Assisted Membrane Peeling for Vitreoretinal Surgery", in Medical Image Computing and Computer-Assisted Intervention (MICCAI), Beijing, September 2010, p. to appear.

[11] M. Kitagawa, D. Dokko, A. M. Okamura, B. T. Bethea, and D. D. Yuh, "Effect of Sensory Substitution on Suture Manipulation Forces for Surgical Teleoperation," in *Medicine Meets Virtual Reality* 12, 2004, pp. 157-163

[12] T. Akinbiyi, C. E. Reiley, S. Saha, D. Burschka, C. J. Hasser, D. D. Yuh, and A. M. Okamura, "Dynamic Augmented Reality for Sensory Substitution in Robot-Assisted Surgical Systems", in 28*th Annual International Conference of the IEEE Engineering in Medicine and Biology Society*, 2006, pp. 567-570

[13] I. Iordachita, Z. Sun, M. Balicki, J. U. Kang, S. J. Phee, J. Handa, P. Gehlbach, and R. Taylor, "A sub-millimetric, 0.25 mN resolution fully integrated fiber-optic force-sensing tool for retinal microsurgery", *Int J Computer Assisted Radiology and Surgery*, vol. 4-4, pp. 383-390, 2009 PMID: 20033585

[14] Z. Sun, M. Balicki, J. Kang, J. Handa, R. Taylor, and I. Iordachita, "Development and Preliminary Data of Novel Integrated Optical Micro-Force Sensing Tools for Retinal Microsurgery", in *IEEE International Conference on Robotics and Automation—ICRA* 2009, Kobe, Japan, 2009, pp. 1897-1902

[15] B. T. Bethea, A. M. Okamura, M. Kitagawa, T. P. Fitton, S. M. Cattaneo, V. L. Gott, W. A. Baumgartner, and D. D. Yuh, "Application of Haptic Feedback to Robotic Surgery", *Journal of Laparoendoscopic and Advanced Surgical Techniques*, vol. 14-3, pp. 191-195, 2004

[16] R. Kumar, P. Berkelman, P. Gupta, A. Barnes, P. S. Jensen, Louis L. Whitcomb, and R. H. Taylor, "Preliminary Experiments in Cooperative Human/Robot Force Control for Robot Assisted Microsurgical Manipulation", in *IEEE Conference on Robotics and Automation*, San Francisco, 2000, pp. 610-617

[17] S. Prasad, M. Kitagawa, G. S. Fischer, J. Z and, M. A. Talamini, R. H. Taylor, and A. M. Okamura, "A Modular 2-DOF Force-Sensing Instrument for Laparoscopic Surgery", in *Proceedings of the Sixth International Conference on Medical Image Computing and Computer Assisted Intervention—MICCAI* 2003, Montreal, 2003, pp. 279-286

[18] T. Akinbiyi, *Intelligent instruments and visual force feedback in laparoscopic minimally invasive surger*, thesis in Mechanical Engineering, The Johns Hopkins University, Baltimore, Md., 2005.

[19] G. Fischer, T. Akinbiyi, S. Saha, J. Zand, M. Talamini, M. Marohn, and R. Taylor, "Ischemia and Force Sensing Surgical Instruments for Augmenting Available Surgeon Information", in *IEEE International Conference on Biomedical Robotics and Biomechatronics—BioRob* 2006, Pisa, Italy, 2006

[20] J. A. C. Heijmans, L. K. Cheung, and F. P. Wieringa, "Optical fiber sensors for medical applications—Practical engineering considerations", in 4th European Conference of the International Federation for Medical and Biological Engineering ECIFMBE, Antwerp, Belgium, 23-27 Nov. 2008

[21] J. C. Jan Peirsa, Dominiek Reynaerts, a, Hendrik Van Brussela, Paul Herijgersb, Brecht Cortevillea and Sarah Boone, "A micro optical force sensor for force feedback during minimally invasive robotic surgery", *Sensors and Actuators A: Physical*, vol. 115-2-3, pp. 447-455, 21 Sep. 2004

[22] M. S. Mueller, L. Hoffmann, T. S. Buck, and A. W. Koch, "Realization of a fiber-optic force-torque sensor with six degrees of freedom", in Proc. SPIE—Optomechatronic Technologies, San Diego, Calif., 17 Nov. 2008, pp. 72660S-1 to 8. http://dx.doi.org/10.1117/12.807141.

[23] P. Puangmali, H. Liu, K. Althoefer, and L. D. Seneviratne, "Optical fiber sensor for soft tissue investigation during minimally invasive surgery", in IEEE Conference on Robotics and Automation (ICRA), Pasadena, Calif., 19-23 May 2008, pp. 2934-2939

[24] J. Desai, "Design and Development of a 3-Axis MRI-compatible Force Sensor", in ICRA 2010 Workshop on Medical Cyber-Physical Systems Anchorage, 7 May 2010, p. (Abstract in Electronic Proceedings).

[25] M. Tada and T. Kanade, "An MR-Compatible Optical Force Sensor for Human Function Modeling", in Medical Image Computing and Computer-Assisted Intervention—MICCAI 2004, St. Malo, France, September 2004, pp. 129-136.

[26] X. He, *Force Sensing Tool for Retinal Surgery*, MS thesis in Mechanical Engineering (MiMed), T. U. Munich, Munich, 2009.

[27] D. Geib, *Multiplexing of Extrinsic Fabry-Perot Optical Fiber Sensors for Strain Measurements*, thesis in Electrical Engineering, Virginia Polytechnic Institute and State University, 2003.

[28] M. Balicki, J.-H. Han, I. Iordachita, P. Gehlbach, J. Handa, R. H. Taylor, and J. Kang, "Single Fiber Optical Coherence Tomography Microsurgical Instruments for Computer and Robot-Assisted Retinal Surgery", in Medical Image Computing and Computer Assisted Surgery (MICCAI 2009), London 2009, pp. 108-115. PMID: Pending.

[29] J. U. Kang and A. Rodriguez, "Fourier Domain common-path fiber OCT with tunable reference: analysis and optimization", *OSA Technical Digest, CLEO*, p. JtuA55, 2007

[30] X. Liu and J. U. Kang, "Progress toward inexpensive endoscopic high-resolution common-path OCT", in *SPIE Conf. on Optical Fibers and Sensors for Medical Diagnostics and Treatment Applications X*, 2010

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A surgical tool system, comprising:
a surgical tool; and
an interferometry system optically coupled to said surgical tool,
wherein said surgical tool comprises:
a body section;
a sensor section at least one of attached to or integral with said body section; and
a surgical section at least one of attached to or integral with said sensor section at an opposing end of said sensor section from said body section, and
wherein said sensor section comprises:
a monolithic reflective surface; and
a plurality of interferometric optical sensors, each of said plurality of interferometric optical sensors having a partially reflective surface opposing and spaced apart from said monolithic reflective surface, and
wherein, for each of said plurality of interferometric optical sensors, a distance between said partially reflective surface and said monolithic reflective surface changes in response to at least one of a force or a torque when applied to said surgical section of said surgical tool.

2. The surgical tool system according to claim 1, wherein said interferometry system comprises:
an optical transmitter arranged to transmit light to said plurality of interferometric optical sensors;
an optical receiver arranged to detect light returned from said plurality of interferometric optical sensors to provide an output signal; and
a signal processor constructed to communicate with said optical receiver to receive said output signal.

3. The surgical tool system according to claim 2, wherein said signal processor is configured to determine a change in said distance for each of said plurality of interferometric optical sensors from said output signal from said optical receiver and to determine at least one of an applied force, an applied torque or a local temperature change.

4. The surgical tool system according to claim 2, wherein said signal processor is configured to determine a change in said distance for each of said plurality of interferometric optical sensors from said output signal from said optical receiver and to determine an applied force taking into account a local temperature change.

5. The surgical tool system of claim 2, wherein said signal processor is further configured to determine said distance for each of said plurality of interferometric optical sensors based on a phase of said transmitted light and a phase of said returned light for each of said plurality of interferometric optical sensors.

6. The surgical tool system according to claim 1, wherein a space between each of said partially reflective surfaces and said monolithic reflective surface is further defined by a compliant material arranged between said partially reflective surfaces and said monolithic reflective surface such that said compliant material can be compressed and elongated in response to varying forces applied to said surgical section to provide a change in said distance for each of said plurality of interferometric optical sensors.

7. The surgical tool system according to claim 1, wherein said sensor section comprises a compliant component attached on one end to said body section and on an opposing end to said surgical section.

8. The surgical tool system according to claim 7, wherein said compliant component is a micro-machined tube comprising flexures.

9. The surgical tool system according to claim 8, wherein said sensor section further comprises a compliant sealing material disposed in gaps between said flexures of said micro-machined tube.

10. The surgical tool system according to claim 7, wherein said compliant component comprises a material that is substantially transparent to an operating wavelength of said interferometric optical sensor.

11. The surgical tool system according to claim 7, wherein said sensor section further comprises a flexible membrane attached around said compliant component to provide a shield.

12. The surgical tool system according to claim 1, further comprising an optical fiber extending along an internal portion of said body section to said sensor section of said surgical tool.

13. The surgical tool system according to claim 1, further comprising a plurality of optical fibers extending along an internal portion of said body section to said sensor section of said surgical tool.

14. The surgical tool system according to claim 1, further comprising a fiber Bragg grating sensor disposed in said body section to measure bending of at least a portion of said body section of said surgical tool.

15. The surgical tool system according to claim 1, wherein said surgical tool is a micro-surgical tool.

16. The surgical tool system according to claim 15, wherein said micro-surgical tool is one of a needle, a pick, a scalpel, forceps, scissors, or a trocar.

17. The surgical tool system according to claim 1, wherein the interferometry system is a common-path optical coherence tomography system.

18. A surgical tool, comprising:
a body section;
a sensor section at least one of attached to or integral with said body section; and
a surgical section at least one of attached to or integral with said sensor section at an opposing end of said sensor section from said body section,
wherein said sensor section comprises:
a monolithic reflective surface; and
a plurality of interferometric optical sensors, each of said plurality of interferometric optical sensors having a partially reflective surface opposing and spaced apart from said monolithic reflective surface, and
wherein, for each of said plurality of interferometric optical sensors, a distance between said partially reflective surface and said monolithic reflective surface changes in response to at least one of a force or a torque applied to said surgical section of said surgical tool.

19. The surgical tool according to claim 18, wherein a space between each of said partially reflective surfaces and said monolithic reflective surface is further defined by a compliant material arranged between said partially reflective surfaces and said monolithic reflective surface such that said compliant material can be compressed and elongated in response to varying forces applied to said surgical section to provide a change in said distance for each of said plurality of interferometric optical sensors.

20. The surgical tool according to claim 18, wherein said sensor section comprises a compliant component attached on one end to said body section and on an opposing end to said surgical section.

21. The surgical tool according to claim 20, wherein said compliant component is a micro-machined tube comprising flexures.

22. The surgical tool according to claim 21, wherein said sensor section further comprises a compliant sealing material disposed in gaps between said flexures of said micro-machined tube.

23. The surgical tool according to claim 20, wherein said compliant component comprises a material that is substantially transparent to an operating wavelength of said interferometric optical sensor.

24. The surgical tool according to claim 20, wherein said sensor section further comprises a flexible membrane attached around said compliant component to provide a shield.

25. The surgical tool according to claim 18, further comprising an optical fiber extending along an internal portion of said body section to said sensor section of said surgical tool.

26. The surgical tool according to claim 18, further comprising a plurality of optical fibers extending along an internal portion of said body section to said sensor section of said surgical tool.

27. The surgical tool according to claim 18, further comprising a fiber Bragg grating sensor disposed in said body section to measure bending of at least a portion of said body section of said surgical tool.

\* \* \* \* \*